United States Patent [19]

Hess et al.

[11] Patent Number: 4,628,937
[45] Date of Patent: Dec. 16, 1986

[54] MAPPING ELECTRODE ASSEMBLY

[75] Inventors: Stanley R. Hess; Peter P. Tarjan, both of Miami, Fla.

[73] Assignee: Cordis Corporation, Miami, Fla.

[21] Appl. No.: 637,159

[22] Filed: Aug. 2, 1984

[51] Int. Cl.[4] .............................................. A61B 5/04
[52] U.S. Cl. ................... 128/642; 128/644; 128/798
[58] Field of Search ............... 128/639, 642, 644, 1 D, 128/668, 695–696, 784, 798, 736

[56] References Cited

U.S. PATENT DOCUMENTS

| 3,699,813 | 10/1972 | Lamb | 128/736 |
| 3,812,861 | 5/1974 | Peters | 128/798 |
| 3,827,426 | 8/1974 | Page et al. | 128/1 D |
| 3,830,224 | 8/1974 | Vanzetti et al. | 128/736 |
| 3,971,363 | 7/1976 | Fletcher et al. | 128/695 |
| 4,030,509 | 6/1977 | Heilman et al. | 128/784 X |
| 4,172,451 | 10/1979 | Kline | 128/642 |
| 4,354,509 | 10/1982 | Strahwald et al. | 128/639 X |
| 4,510,939 | 4/1985 | Brenman et al. | 128/639 |
| 4,522,212 | 6/1985 | Gelinas et al. | 128/784 X |

FOREIGN PATENT DOCUMENTS 0611617 6/1978 U.S.S.R. ............................... 128/1 D

Primary Examiner—Kyle L. Howell
Assistant Examiner—Angela D. Sykes
Attorney, Agent, or Firm—Lockwood, Alex, Fitzgibbon & Cummings

[57] ABSTRACT

A set of electrodes are provided, preferably in a symmetrical array, which electrodes are mounted within a pliable mounting cup that is capable of conforming to the shape and size of various surfaces of body organs, such as the heart. The pliable cup is capable of both epicardial and endocardial types of mapping procedures, each electrode being connected to a thin insulated wire that joins similar wires in a generally centrally located trunk portion of the cup, and a cable containing the thus bundled wires depends from the trunk portion for connection to a suitable data display and/or recording system.

7 Claims, 20 Drawing Figures

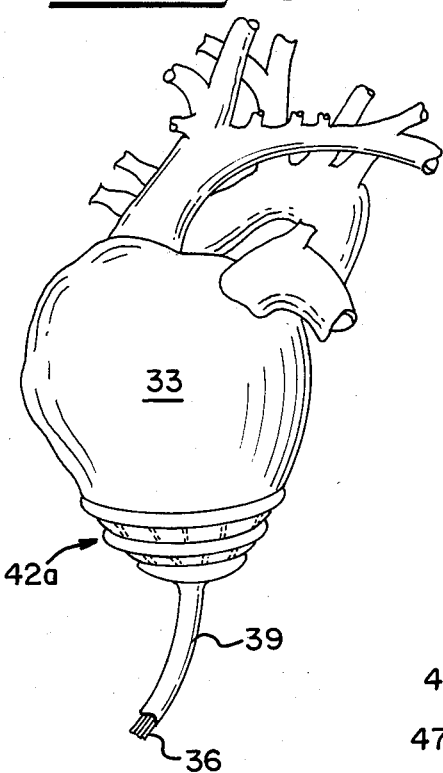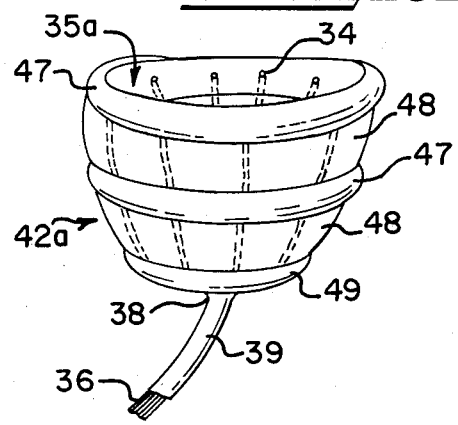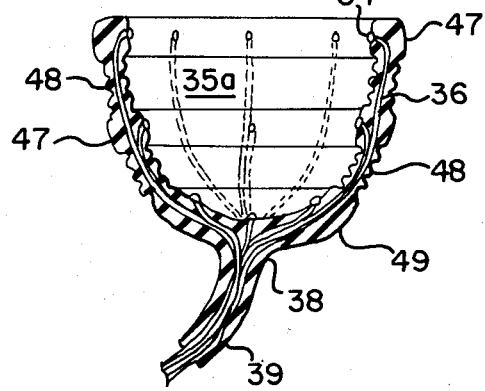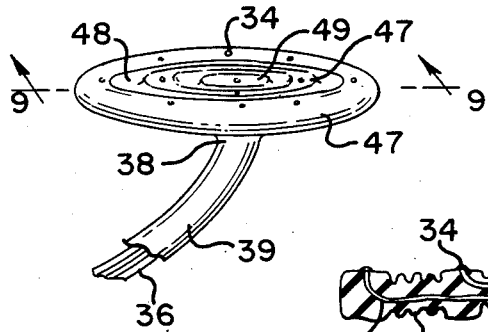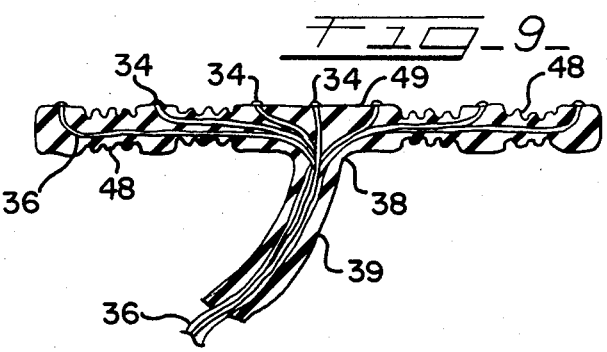

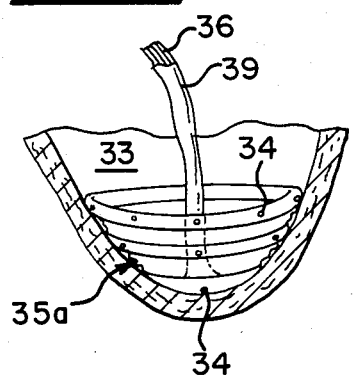
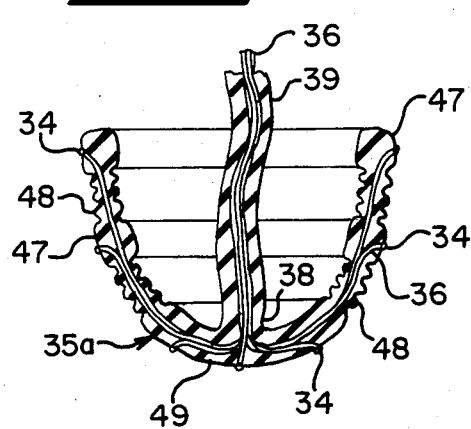
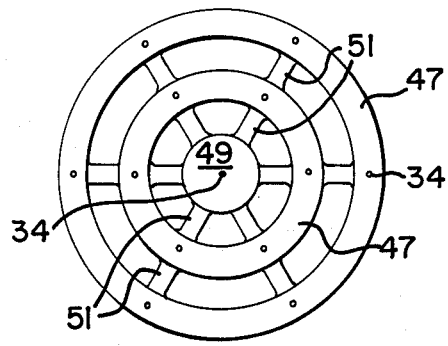
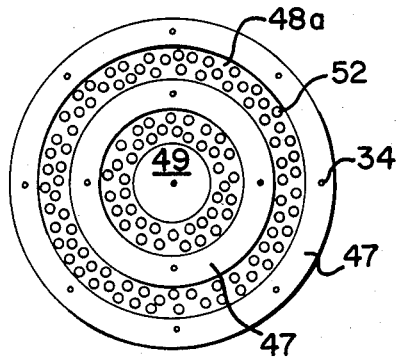
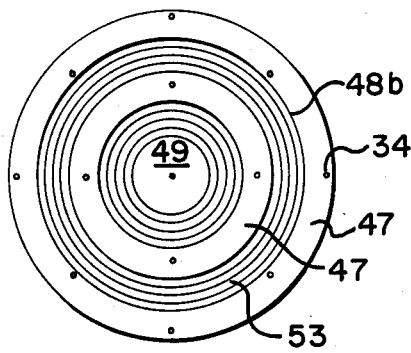

MAPPING ELECTRODE ASSEMBLY

BACKGROUND OF THE INVENTION

This invention generally relates to cardiac mapping, more particularly to electrode sets and assemblies for conducting epicardial and/or endocardial mapping. In an important aspect of this invention, the electrode set is arranged in a manner such that the configuration of the set will generally conform to the portion of the heart that is being mapped, including generally convex and concave portions such as the apical portion thereof. In another important aspect of the mapping electrode assembly according to this invention, the electrodes are provided in a symmetrical array such that the assembled electrode set can be rotated by a predetermined angular amount, for example 60°, without substantially varying the electrode pattern.

Mapping electrode sets for epicardial and endocardial mapping of heart signals have been provided in the past. Typically, these mapping electrode sets are utilized during cardiac surgery in order to sense the cardiac signal and report it to the surgical team through appropriate display and/or print out devices. The surgical team may observe the reported data and immediately utilize same in connection with a surgical procedure, or the data may be collected for subsequential analysis. Such mapping involves timing that is based upon the leading edge of an excitation wave through conductive tissue of the heart. Generally, mapping procedures include the induction of tachycardia while the mapping electrode set is in place, which means that mapping speed and efficiency is extremely important during these procedures.

One characteristic of a mapping electrode set that can interfere with mapping speed and efficiency is the inability of the electrode set to be manipulated such that electrodes are positioned at the desired cardiac location. In the past, the electrodes of a mapping set typically have been generally stationarily mounted with respect to each other, whereby it is not possible to substantially modify the mapping surface to which the electrodes are mounted. Many such mapping surfaces are generally flat, and it is not possible to simultaneously engage all of the electrodes of such a mapping surface with a concave or convex tissue surface being mapped. Even when such electrode sets are mounted into a mapping surface having a generally curved configuration, the particular curved configuration does not always adequately conform to the concave or convex tissue surface to which it is applied, with the result that all of the electrodes needed by the surgeon cannot simultaneously contact the cardiac tissue being mapped. For example, a substantially flat electrode set cannot be satisfactorily used for mapping the apical portion of the heart. Non-contact of an electrode contributes to inadequate data being reported relative to the time and the direction of propagation along and activation of a particular pathway. If the tissue area being mapped is generously curved, such as in an apical region of the heart, this non-contact of electrodes will often prevent any truly useful mapping of such an area.

Also, it often becomes necessary, especially when mapping tissue areas that are difficult to reach, to maneuver the mapping electrode assembly in order to precisely locate same. Such manipulation can be hampered by connector leads and the like of the mapping device, and minimizing the manipulation of the electrode mounting structure that is needed for a particular placement of the electrode set can be advantageous in many instances.

There is accordingly a need for a mapping electrode set assembly that is capable of conforming to the configurations of body organs, particularly the apical area of the heart such that the electrodes can simultaneously contact the heart tissue. It is also desirable to provide a mapping electrode system wherein the electrode set is positioned in a symmetrical array in order to provide a plurality of substantially identical electrode orientations that can be located at a desired position by a minimum of manipulation.

SUMMARY OF THE INVENTION

By virtue of the present invention, an electrode set assembly is provided wherein the electrodes are mounted within a pliable mounting cup, and the electrodes are attached to leads that are bundled together and fed through a trunk of the pliable mounting cup, whereby the electrodes are controllably movable with respect to each other such that the electrode set assembly is conformable to a variety of shaped surfaces. In an important aspect of this invention, the electrodes are in an arrangement that provides a symmetrical electrode array on a surface of the pliable mounting cup.

It is accordingly a general object of the present invention to provide an improved mapping electrode assembly and method.

Another object of this invention is to provide an improved cardiac mapping electrode set assembly and method that includes an electrode mounting assembly having a variable configuration for conforming to cardiac surfaces.

Another object of this invention is to provide improved epicardial and/or endocardial mapping assembly and method that provides sensitive detection of wavefront activity on surfaces that are concave or convex.

Another object of the present invention is to provide an improved mapping electrode set assembly having the electrodes oriented in a conformable symmetrical array.

BRIEF DESCRIPTION OF THE DRAWINGS

These and other objects of the present invention will be apparent from the following description of this invention, taken in conjunction with the accompanying drawings, wherein:

FIG. 5 is a generally elevational illustration of another mapping electrode assembly according to this invention, shown in its epicardial mapping orientation;

FIG. 6 is a perspective view of the electrode assembly of FIG. 5;

FIG. 7 is a longitudinal cross sectional view of the assembly shown in FIG. 6;

FIG. 8 is a perspective view of the assembly of FIG. 6 wherein the assembly is collapsed;

FIG. 9 is a cross sectional view along the line 9—9 of FIG. 8;

FIG. 10 is a perspective illustration of the assembly of FIG. 6 when same has an endocardial mapping orientation;

FIG. 11 is a longitudinal sectional view through the mapping assembly as shown in FIG. 10; and FIG. 12, FIG. 13, FIG. 14, FIG. 15, FIG. 16, FIG. 17, FIG. 18, FIG. 19 and FIG. 20 are plan views of various embodiments of electrode assemblies having differing electrode positions and showing several different symmetrical electrode arrays.

DESCRIPTION OF THE PREFERRED EMBODIMENTS

Figure 1:
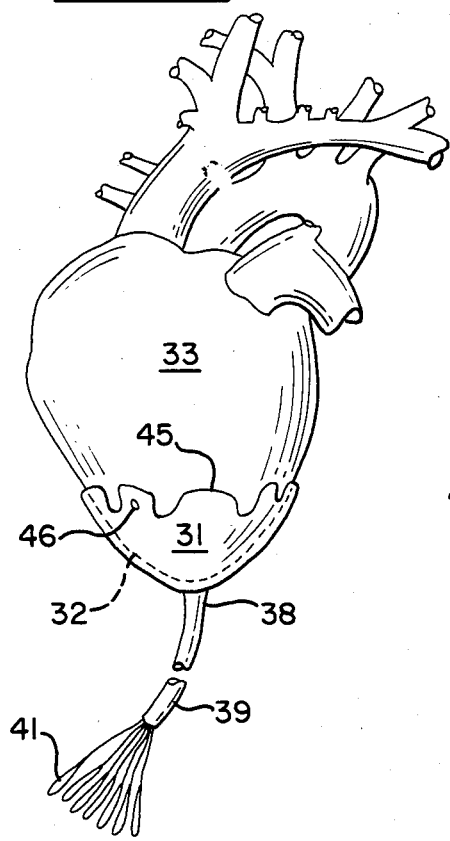
FIG. 1 is a generally elevational illustration of the preferred mapping electrode assembly according to this invention, showing an epicardial mapping application of the electrode assembly.
Figure 2:
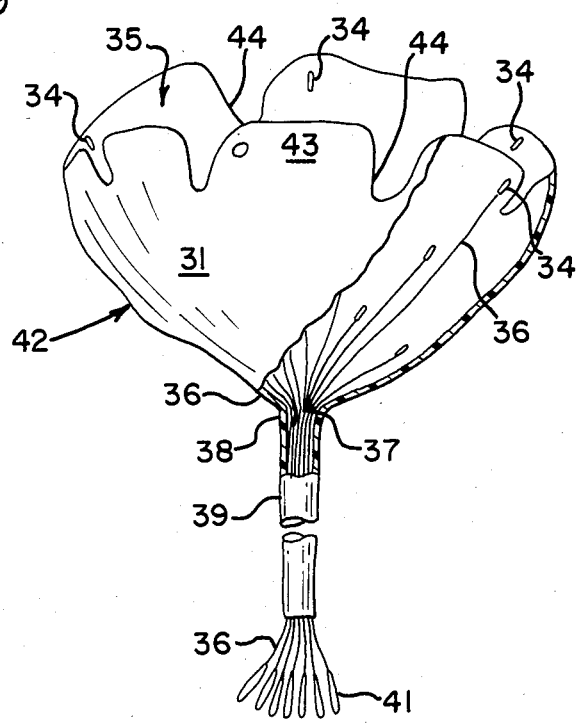
FIG. 2 is a perspective view of the electrode assembly illustrated in FIG. 1.
Figure 4:
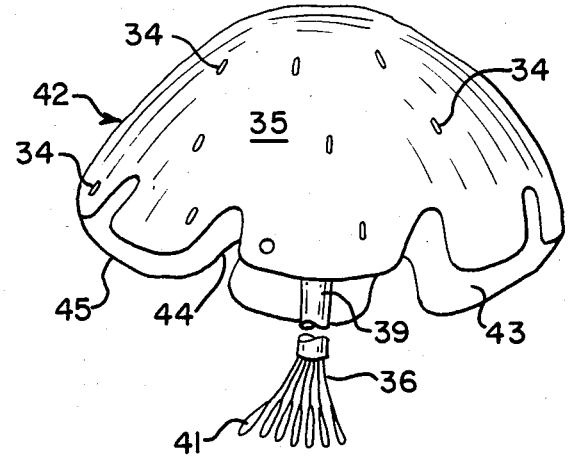
FIG. 4 is a perspective view of the electrode assembly of FIG. 2 when in its orientation for endocardial mapping.

A mapping assembly, generally designated as 31, is illustrated in FIG. 1 when used for mapping an apex 32 of a human heart 33, and a more detailed illustration of the mapping assembly 31 is shown in FIG. 2. A plurality of electrodes 34 are mounted so that they are exposed on the administration surface 35 of the mapping assembly 31. This administration surface 35 is generally concave and is the substantially internal portion of the mapping assembly 31 when it is in its epicardial mapping orientation shown in FIGS. 1 and 2. Administration surface 35 is generally convex and substantially external when the mapping assembly 31 is in its endocardial mapping orientation that is illustrated in FIG. 4.

Each electrode 34 is soldered, spot welded or otherwise affixed to an insulated wire or flexible lead 36. Some of these wires or leads 36 are illustrated in FIG. 2, while others are not shown in order to maintain drawing clarity. Insulated wires or leads generally converge to form a bundle 37 at a trunk portion 38 of the mapping assembly 31. Trunk portion 38 extends to a cable 39, and each wire 36 terminates with a connector 41 for providing electrical communication with a suitable monitoring and/or data recording device.

With more particular reference to the administration surface 35, same is a surface of a pliable mounting cup, generally designated as 42. The pliable mounting cup 42 is made of a very flexible material that is suitable for medical uses, including synthetic rubber materials, Silastic or the like. Most advantageously, such material is relatively thin in order that the mounting cup 42 has enough pliability so that the administration surface 35 is generally concave when oriented as illustrated in FIG. 2, while the mounting cup 42 can be bent on itself to the generally convex configuration illustrated in FIG. 4. Preferably, the pliable mounting cup 42 is generally lobular and includes a plurality of lobes 43 and fissures 44. Each fissure 44 extends from the remote, free edge 45 of the pliable mounting cup 42 and assists in providing the pliability characteristics of the cup 42 by enhancing the ability of the surgeon to vary the circumference of the free edge 45 and the distance between electrodes. If desired, a hole 46 or similar indicator may be provided in order to distinquish and identify one or more of the lobes 43.

Pliable mounting cup 42a as generally illustrated in FIG. 5 includes electrodes 34 and insulated wires or leads 36 passing through cable 39. Electrodes 34 are mounted on administration surface, generally designated as 35a, such that the electrodes 34 are exposed and can be brought into contact with heart 33 or the like, including an apex 32 thereof.

The pliable mounting cup 42a of this embodiment includes one or more rings 47 which need not be as pliable and bendable as the pliable mounting cup 42 of the embodiment of FIGS. 1 through 4. This is possible because the rings 47 are joined by flexible membranes 48 such that the pliable mounting cup 42a has a generally telescoping construction. Preferably, the centralmost ring 49 is a pliable pad that is generally integral with the trunk portion 38, and the centralmost electrodes 34 are supported by the centralmost ring or pliable pad 49. With this structure, the pliable mounting cup 42a can generally telescope from a flattened position (FIGS. 8 and 9) to a generally endocardial mapping position which generally encloses a portion of the cable 39 (FIGS. 10 and 11), as well as telescope in a generally epicardial direction away from the cable 39 (FIGS. 5, 6 and 7).

With more particular reference to the flexible membranes 48, these may be generally continuous as illustrated in FIGS. 5 through 11. Their flexibility can be enhanced. For example, such may include a plurality of generally radially extending spokes 51 as illustrated in FIG. 12, which generally enhances the pliability of the connection between the rings 47 and/or between a ring 47 and the centralmost ring 49. Another flexible membrane 48a includes perforations 52, as shown in FIG. 13. FIG. 14 illustrates flexible membrane 48b which includes a plurality of generally concentric bands 53, which provide a somewhat accordion-like structure. These various configurations of the flexible membrane can be combined as desired in order to provide a pliable mounting cup 42a having the extent of pliability needed. For example, spokes 51 could be perforated and/or banded.

Rings 47 and 49 should be fabricated of somewhat flexible material that is suitable for medical uses, such as silicone rubber or the like. Flexible membranes 48, 48a, 48b typically will be molded together with the rings 47, 49.

The various electrodes in any of the embodiments according to this invention are preferably mounted in a symmetrical array in order to provide a plurality of sub-sets of substantially identically positioned electrodes, each sub-set being at a variety of angular spacings around the pliable cup. Such symmetrical array may be, for example, hexagonal, pentagonal, square, triangular or the like. One, two, or more rings 47 can be provided as desired.

Figure 3:
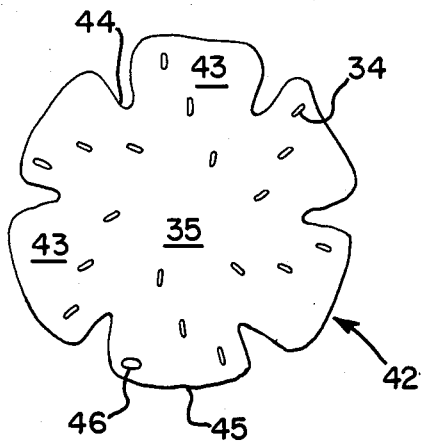
FIG. 3 is a top plan view of the electrode assembly shown in FIG. 2.
Figure 15:
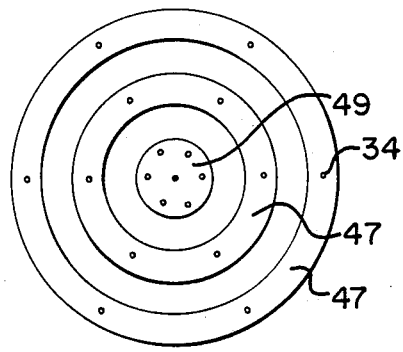
Figure 16:
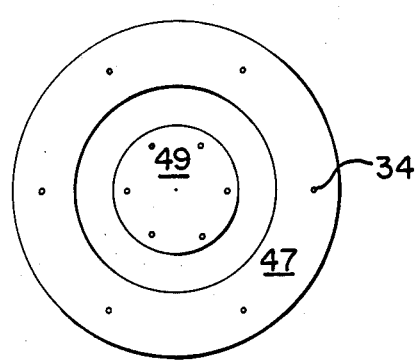
Figure 17:
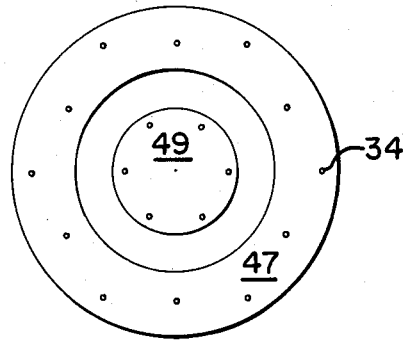
Figure 18:
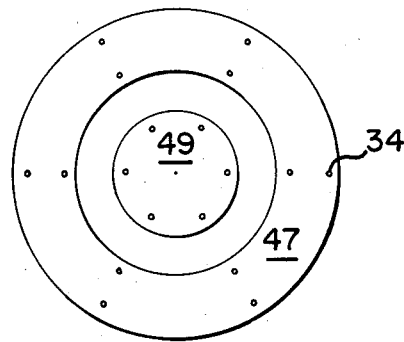
Figure 19:
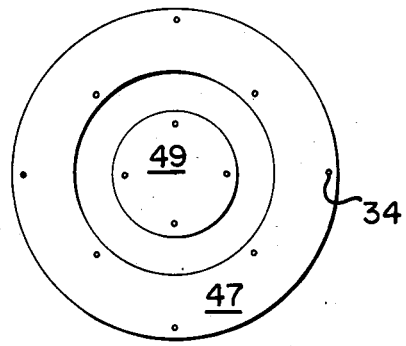
Figure 20:
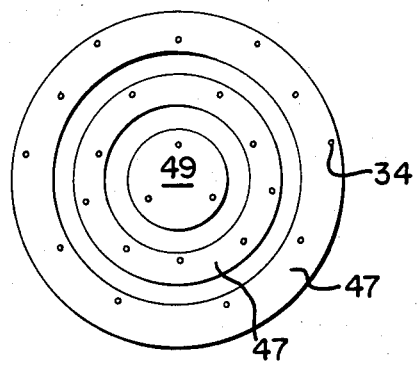

The array illustrated in FIG. 3 is generally hexagonal to the extent that substantially the same electrode configuration is provided each time that the mapping assembly 31 is rotated 60°. FIG. 12 illustrates a somewhat different hexagonal array. FIGS. 13 and 14 each provide a generally square array having generally identically oriented electrodes within each quadrant thereof. FIG. 15 provides a generally hexagonal orientation and includes two rings 47 and a plurality of electrodes 34 in the pliable pad 49, while FIG. 16 is similarly hexagonal, except it includes only a single ring 47. FIG. 17 is similar to FIG. 16, except each hexagonal portion includes an additional electrode. FIG. 18 is also hexagonally oriented, and FIG. 19 illustrates a generally square configuration similar to that of FIG. 14, except same has only a single ring 47. FIG. 20 illustrates a triangular array.

It is to be appreciated that this invention can be embodied in various forms and therefor is to be construed and limited only by the scope of the appended claims.

We claim:

1. A conforming cardiac mapping electrode set assembly, comprising:
   a pliable electrically insulative mounting cup having electrodes mounted therein, said electrodes being exposed on an electrically insulative administration surface of the pliable mounting cup for conforming contact with cardiac tissue, said pliable mounting cup having a shape that is variable between a concave orientation of the administration surface and a convex orientation of the administration surface;
   a trunk portion generally centrally disposed with respect to said pliable mounting cup, said trunk portion having a cable depending therefrom;
   an insulated wire connected to each said electrode, each said insulated wire passing through said generally centrally disposed trunk portion and through said cable, said insulated wires being insulated from each other; and
   said electrodes of said pliable mounting cup being controllably movable with said pliable electrically insulative mounting cup to provide an array of electrodes on the electrically insulative administration surface that is conformable to a convex surface of the cardiac tissue and that is also conformable to a concave surface of the cardiac tissue.

2. The conforming electrode set assembly according to claim 1, wherein said electrodes of said pliable mounting cup are oriented in a symmetrical array, said symmetrical array including a plurality of sub-sets of electrodes, each sub-set having its electrodes generally identically positioned.

3. The conforming mapping electrode set assembly according to claim 1, wherein said pliable mounting cup is generally lobular and includes a plurality of lobes and fissures.

4. The conforming mapping electrode set assembly according to claim 1, wherein said pliable mounting cup includes a plurality of generally concentric rings joined by a flexible membrane, said flexible membrane having a flexibility that is greater than that of said generally concentric rings.

5. The conforming mapping electrode set assembly according to claim 4, wherein said flexible membrane includes a plurality of generally radially extending spokes.

6. The conforming mapping electrode set assembly according to claim 4, wherein said flexible membrane is perforated.

7. The conforming mapping electrode set assembly according to claim 4, wherein said flexible membrane includes a plurality of generally concentric bands.

* * * * *